US00PP19786P2

(12) United States Plant Patent
Danziger

(10) Patent No.: US PP19,786 P2
(45) Date of Patent: Mar. 3, 2009

(54) ***SUTERA* PLANT NAMED 'DANCOP26'**

(50) Latin Name: *Sutera cordata*
Varietal Denomination: Dancop26

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,424

(22) Filed: Jan. 11, 2008

(51) Int. Cl.
*A01H 5/00* (2006.01)

(52) U.S. Cl. ..... Plt./485
(58) Field of Classification Search ..... Plt./485
See application file for complete search history.

*Primary Examiner*—Annette H Para
*Assistant Examiner*—S. B. McCormick Ewoldt

(57) ABSTRACT

A new and distinct *Sutera* cultivar named 'DANCOP26' is disclosed, characterized by having large, clear pink flowers, a compact, trailing plant habit and continuous flowering. The new variety is a *Sutera,* normally produced as an outdoor garden or container plant.

2 Drawing Sheets

Latin name of the genus and species: *Sutera cordata.*
Variety denomination: 'DANCOP26'.

BACKGROUND OF THE INVENTION

The new *Sutera* cultivar is a product of a planned breeding program conducted by the inventor, Gabriel Danziger, in Moshav Mishmar Hashiva, Israel. The objective of the breeding program was to produce plants of *Sutera cordata* with compact habits and large flowers. The seed parent is the unpatented, proprietary seedling variety referred to as *Sutera cordata* 'cv.5-259.' The pollen parent is unknown, as 'Dancop26' is a result of a planned open pollination in which the pollen parent is impossible to distinguish. The new variety was discovered in May 2006 by the inventor in a group of seedlings resulting from that crossing, in Moshav Mishmar Hashiva, Israel.

Asexual reproduction of the new cultivar 'DANCOP26' by vegetative cuttings was first performed at a commercial greenhouse in Moshav Mishmar Hashiva, Israel in June 2006 and has shown that the unique features of this cultivar are stable and reproduced true to type in successive generations.

SUMMARY OF THE INVENTION

The cultivar 'DANCOP26' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP26'. These characteristics in combination distinguish 'DANCOP26' as a new and distinct *Sutera* cultivar:

1. Compact plant habit.
2. Very large flowers.
3. Unique pink flower coloration.
4. Trailing plant habit.

Plants of the new cultivar 'DANCOP26' are similar to plants of the parent, *Sutera cordata* 'cv.5-259' in most horticultural characteristics, however, plants of the new cultivar 'DANCOP26' produce uniform, clear pink flowers, while plants of 'cv 5-259' produce blurred pink flowers of various shades. Additionally, plants of 'DANCOP26' have a more trailing habit than the female parent.

Plants of the new cultivar 'DANCOP26' are similar to plants of the commercial variety 'DANCOP19,' U.S. Plant Pat. No. 18,116 in most horticultural characteristics, however, plants of the new cultivar 'DANCOP26' have larger flowers, of a lighter pink. The new variety also has a more trailing plant habit and larger leaves than 'DanCOP19.'

BRIEF DESCRIPTION OF THE PHOTOGRAPH

Figure 1:
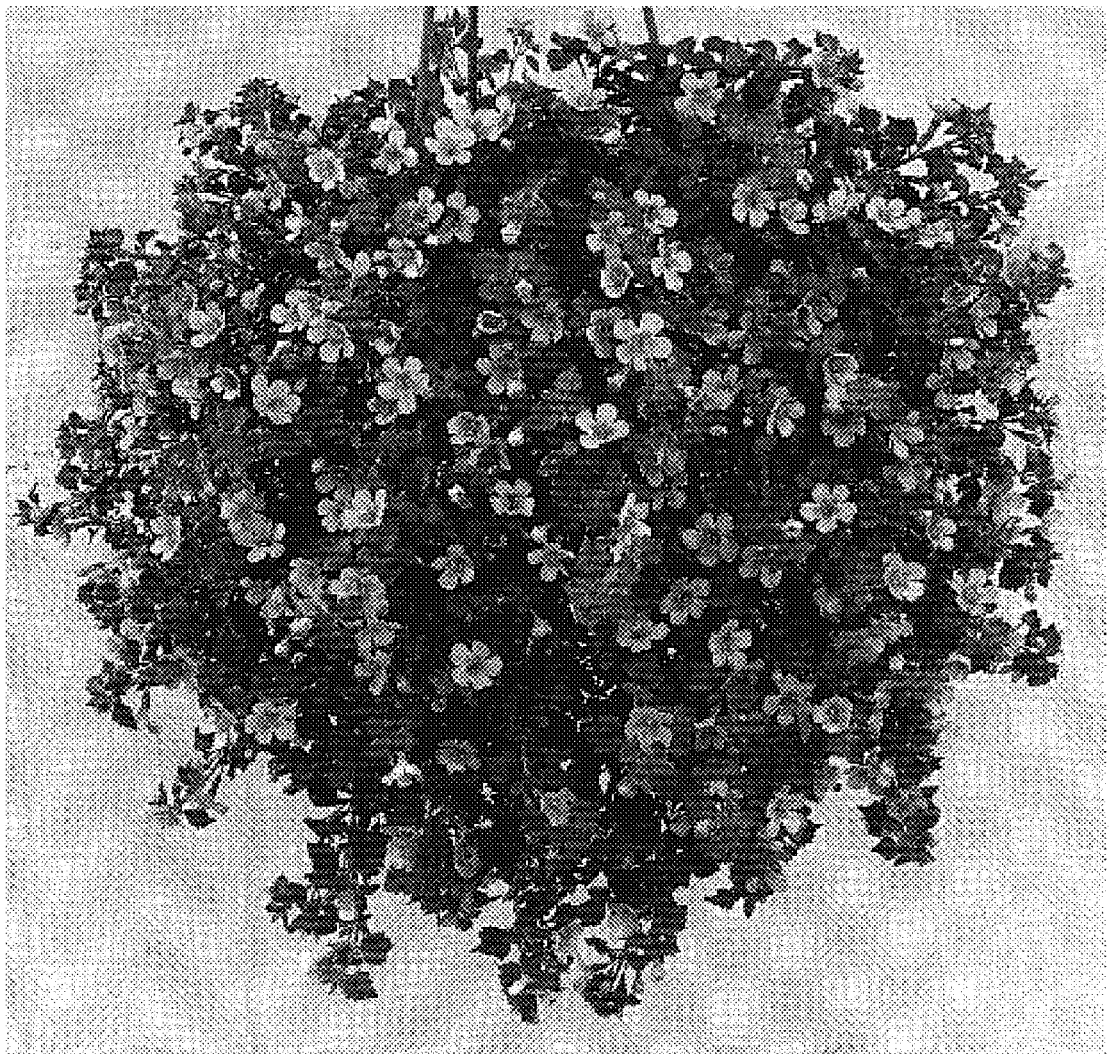

The accompanying photograph in FIG. 1 illustrates in full color a typical plant of 'DANCOP26' grown in a greenhouse, in a 13 cm basket. Age of the plant photographed is approximately 3 months from a rooted cutting.

Figure 2:
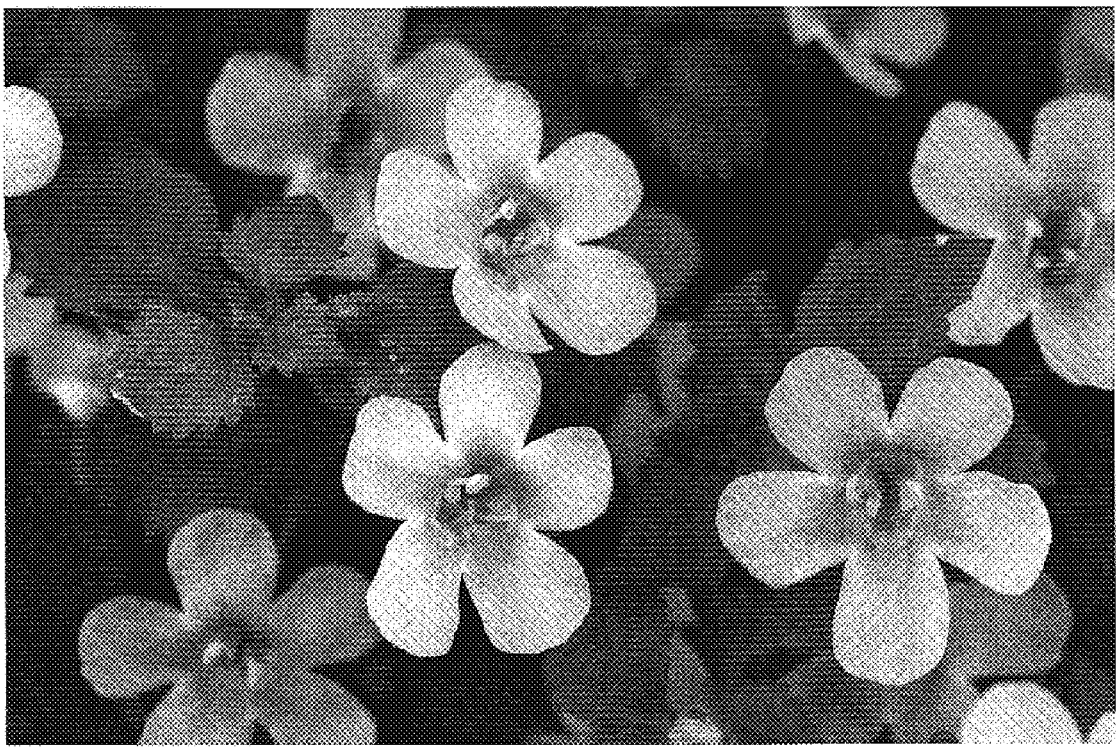

FIG. 2 illustrates in full color a close up of a typical bloom of 'DANCOP26.' The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANCOP26' plants grown in a greenhouse in Moshav Mishmar Hashiva, Israel. The growing temperature ranged from 18° C. to 24° C. The greenhouse is subject to partial shade. General light conditions are bright, normal sunlight, with some shade during the brightest part of the day. Measurements and numerical values represent averages of typical plant types.

Botanical classification: *Sutera cordata* cultivar 'DANCOP26.'

PROPAGATION

Time to Initiate Roots: About 7 to 10 days at approximately 18° C.

Root Description: Fine, densely fibrous.

PLANT

Growth Habit: Mounding annual.
Pot size of plant described: 13 cm.
Age of Plant Described: Approximately 90 days from a rooted cutting.
Height:
*To top of flowers.*—Approximately 8 cm.
Plant Spread: Approximately 55 cm.
Growth Rate: Moderate.
Branching Characteristics: Very well-branched.
Length of Primary Lateral Branches: Approximately 50 cm.
Diameter of Lateral Branches: Approximately 0.2 cm
Quantity of Primary Lateral Branches: About 8.
Characteristics of Primary Lateral Branches:
*Form.*—Cylindrical.
*Diameter.*—Approximately 0.2 cm.
*Color.*—Near RHS Yellow-Green 146A.
*Texture.*—Velvety.
*Strength.*—Strong.
Internode length: Approximately 2 cm.

FOLIAGE

Leaf:
*Arrangement.*—Opposite.
*Quantity.*—Approximately 100 per branch.
*Average length.*—Approximately 2 cm.
*Average width.*—Approximately 1.5 cm.
*Shape of blade.*—Ovate.
*Apex.*—Acute.
*Base.*—Acuminate.
*Margin.*—Serrate.
*Texture of top surface.*—Velvety.
*Pubescence.*—Slightly pubescent.
*Aspect.*—Slanted downward.
*Color.*—Young foliage upper side: Near RHS Green 137B. Young foliage under side: Near RHS Green 137C. Mature foliage upper side: Near RHS Yellow-Green 147A. Mature foliage under side: Near RHS Yellow-Green 147B.
*Venation.*—Type: Pinnate. Venation color upper side: Near RHS Yellow-Green 147B. Venation color under side: Near RHS Yellow-Green 147A.
*Petiole.*—Length: Approximately 0.7 cm. Diameter: Approximately 0.1 cm. Color: Near RHS Green 137C. Texture: Velvety.

FLOWER

Natural flowering season: Freely flowering under outdoors growing conditions with substantially continuous blooming from spring through autumn. Year round in greenhouse environment, or under warm conditions and high sunlight. Flowering begins approximately 4 weeks after planting a rooted cutting.
Inflorescence and flower type and habit: Individual flowers are typical scrophulariaceae shape, 2-lipped, 5-petaled solitary flowers, fused at base, occurring in the leaf axis, on a terminal raceme.
Rate of flower opening: 3 days from bud to fully opened flower.
Flower Longevity on Plant: Individual flowers last 7 days on the plant.
Quantity of flowers: About 200 open blooms per plant.
Flower Form: Salverform.
Flower size:
*Diameter.*—Approximately 1.8 cm.
*Length.*—Approximately 1.5 cm.
*Corolla tube diameter.*—Approximately 0.3 cm.
Corolla/Petals:
*Arrangement.*—5 rounded and gameopetalous petals.
*Lobe length.*—About 0.7 cm.
*Lobe width.*—About 0.6 cm.
*Quantity.*—5.
*Texture.*—Velvety.
*Lobe apex.*—Rounded.
*Lobe shape.*—Rounded.
*Margin.*—Entire.
*Aspect.*—Slanted upward.
Color:
*When opening.*—Upper surface: Near RHS Purple N78C. Lower surface: Near RHS Purple 76A.
*Fully opened.*—Upper surface: Near RHS Purple N78D. Lower surface: Near RHS Purple 76A.
*Corolla tube color.*—Near RHS yellow-Green 154C.
Bud:
*Shape.*—Slightly flattened sphere.
*Length.*—Approximately 1 cm.
*Diameter.*—Approximately 0.4 cm.
*Color.*—Near RHS Purple N78C.
Calyx/Sepals:
*Quantity per flower.*—5, fused at base.
*Shape.*—Linear.
*Length.*—Approximately 0.5 cm.
*Width.*—Approximately 0.1 cm
*Apex.*—Acute.
*Base.*—Fused.
*Margin.*—Entire.
*Texture.*—Velvety.
*Color.*—Upper Surface: Near RHS Yellow-Green 146B. Lower Surface: Near RHS Yellow-Green 146B.
Peduncle: None.
Pedicel:
*Length.*—Approximately 0.7 cm.
*Diameter.*—Approximately 0.1 cm.
*Color.*—Near RHS Yellow-Green 146B.
*Orientation.*—Slanted upward at an angle of about 45°.
*Pubescence.*—Slight.
Fragrance: None.

REPRODUCTIVE ORGANS

Stamens:
*Number.*—4.
*Filament length.*—Approximately 0.9 cm.
Anthers:
*Shape.*—Cylindrical.
*Length.*—Approximately 0.1 cm.
*Color.*—Near RHS Yellow 13A.
*Pollen.*—Color. Near RHS Yellow 13B. Quantity: Moderate.
Pistil:
*Number.*—1.
*Length.*—Approximately 1.2 cm.

*Style.*—Length: Approximately 1.2 cm. Color: Near RHS Green-Yellow 1B.

*Stigma.*—Shape: Round. Color: Near RHS Green 153A. Ovary Color: Near RHS Green 143C.

OTHER CHARACTERISTICS

Seeds and fruits: Not observed and not commercially important.

Disease/pest resistance: Neither resistance nor susceptibility to pathogens and pests common to *Sutera* have been observed.

Temperature tolerance: The new variety tolerates temperatures between 5 to 35° C.

What is claimed is:

1. A new and distinct cultivar of *Sutera* plant named 'DANCOP26' herein illustrated and described.

* * * * *